(12) United States Patent
Solazzo

(10) Patent No.: US 7,278,987 B2
(45) Date of Patent: Oct. 9, 2007

(54) ERGONOMIC UROLOGICAL CATHETERIZATION/IRRIGATION TRAY

(76) Inventor: Anthony Solazzo, 100 Acorn Rd., Watchung, NJ (US) 07069

( * ) Notice: Subject to any disclaimer, the term of this patent is extended or adjusted under 35 U.S.C. 154(b) by 11 days.

(21) Appl. No.: 10/888,659

(22) Filed: Jul. 9, 2004

(65) Prior Publication Data

US 2006/0009742 A1   Jan. 12, 2006

(51) Int. Cl.
| | | |
|---|---|---|
| *A61B 19/00* | (2006.01) | |
| *A61M 1/00* | (2006.01) | |
| *B65D 69/00* | (2006.01) | |
| *E03C 1/01* | (2006.01) | |
| *A61M 29/00* | (2006.01) | |

(52) U.S. Cl. .................... 604/356; 206/571; 604/319; 4/640

(58) Field of Classification Search ............. 604/356, 604/317, 319, 326; 206/571; 4/640, 650, 4/660
See application file for complete search history.

(56) References Cited

U.S. PATENT DOCUMENTS

| | | | | |
|---|---|---|---|---|
| 2,032,593 | A * | 3/1936 | Rice ........................... 108/18 |
| 2,563,060 | A * | 8/1951 | O'Neill ......................... 108/6 |
| 2,783,109 | A * | 2/1957 | Frey ............................ 108/43 |
| 3,166,189 | A * | 1/1965 | Disston ........................ 206/364 |
| 3,329,261 | A * | 7/1967 | Serany, Jr. et al. .......... 206/229 |
| 3,532,336 | A * | 10/1970 | Baker ........................... 5/650 |
| 3,795,015 | A * | 3/1974 | Talge et al. ................. 4/420.3 |
| 3,851,649 | A | 12/1974 | Villari |
| 4,160,505 | A | 7/1979 | Rauschenberger |
| 4,226,328 | A * | 10/1980 | Beddow ........................ 206/364 |
| 4,503,864 | A * | 3/1985 | Powers ......................... 600/573 |
| 4,595,102 | A * | 6/1986 | Cianci et al. ................ 206/572 |
| 4,635,913 | A * | 1/1987 | Rothman ....................... 5/658 |
| 4,752,293 | A * | 6/1988 | Smith .......................... 604/322 |
| 4,811,847 | A | 3/1989 | Reif |
| 4,925,448 | A * | 5/1990 | Bazaral ........................ 604/171 |
| 5,242,398 | A | 9/1993 | Knoll |
| 5,339,955 | A * | 8/1994 | Horan et al. ................. 206/370 |
| 5,383,411 | A * | 1/1995 | Tomaka et al. .............. 108/129 |
| 5,438,938 | A * | 8/1995 | Meeker et al. ................ 108/91 |
| 5,586,163 | A * | 12/1996 | Goldstein ..................... 378/204 |
| 5,697,921 | A * | 12/1997 | Blair ........................... 604/317 |
| 5,792,125 | A * | 8/1998 | Webb ........................... 604/317 |
| 6,012,586 | A * | 1/2000 | Misra .......................... 206/571 |
| 6,090,075 | A | 7/2000 | House |
| 6,485,438 | B1 * | 11/2002 | Minue ......................... 600/573 |
| 2003/0056285 | A1 * | 3/2003 | Pollastri et al. .............. 4/574.1 |
| 2005/0205450 | A1 * | 9/2005 | Leitch ......................... 206/438 |

* cited by examiner

*Primary Examiner*—Tatyana Zalukaeva
*Assistant Examiner*—Paula L. Craig
(74) *Attorney, Agent, or Firm*—Kenneth P. Glynn, Esq.

(57) ABSTRACT

The present invention relates to an ergonomic urological catheterization/irrigation tray. The tray includes a tray structure having a recessed area that includes at least a bottom, opposite side walls, a front and a back, wherein the front has a first width of a predetermined dimension and the back has a second width of a predetermined dimension less then the first width, such that the recessed area is wider at the front than it is at the back. The recessed area has at least one drain located at a lower area thereof. The tray further includes a top flange extending at least outwardly each of the opposite side walls, wherein a user may rest the flange on front upper portions of legs when in a supine position, for urinary bladder evacuation into the tray. Surgical kits contain the aforementioned tray and specified components.

16 Claims, 8 Drawing Sheets

ERGONOMIC UROLOGICAL
CATHETERIZATION/IRRIGATION TRAY

BACKGROUND OF THE INVENTION

1. Field of the Invention

The present invention is an ergonomic urological catheterization/irrigation tray. The tray has a shape that will fit between the legs of a patient, has a contoured or terraced recess so as to create a tapered wall/bottom arrangement (easier to rest atop upper leg areas when the patient is seated). Further, the present invention has support wings, drainage accommodations, and accessory accommodations.

2. Information Disclosure Statement

The following prior art is representative of the state of the art in the field of catheterzation trays, kits and systems:

U.S. Pat. No. 3,851,649 discloses a catheterization package comprising a rigid container including a generally flat rear panel and a front panel parallel to and spaced from one another with a top wall, side walls and a bottom wall extending there between, said front panel having a recessed catheter drainage port with a catheter connected thereto adjacent the upper and one side wall of said container, said catheter being positioned within an open sided recess in said one wall with said port at one end thereof a container drainage port having a removable closure positioned in said front wall adjacent the upper and the other side wall of said container, a plurality of discrete recesses in said front wall carrying therein a plurality of catheterization components and cover means releasable retained adjacent said front wall for retaining said components including said catheter within their individual recesses, said container upon removal of said components being utilize for collection of liquid drained through said catheter.

U.S. Pat. No. 4,160,505 discloses a urethral catheterization tray providing a sterile, self-contained catheterization package and work area.

U.S. Pat. No. 4,811,847 discloses a package for an urinary catheter that consists of a generally rectangular tray with an open top, to which a peel-back cover is bonded, containing a catheter assembly, a syringe prefilled with bacteriostatic water, and two gloves. The catheter assembly is designed such that a urinary catheter may be simply and efficiently placed into the bladder under sterile conditions. The catheter assembly consists of a heat shrunk seal to hold the end cap, three intermediate caps with antiseptic soaked sponge tips bonded to the ends, and the tube-like guide in proximity therewith. The catheter passes through the guide after removal of the heat shrunk seal and the systematic removal and utilization of the end cap and the three intermediate caps. A protective shroud encloses the distal end of the catheter, as it is bonded to the guide. A biocompatible lubricant is contained between the third intermediate cap and the guide.

U.S. Pat. No. 5,242,398 discloses a catheter and a sheath enclosing the catheter to preserve the sterility thereof, the sheath being provided with a plurality of fold lines which form accordion-like pleats to enable a collapse of the sheath at a point of insertion of the catheter into a patient. The sheath is provided at a distal end of the catheter with a flange for engaging a patient during an insertion of the catheter into the patient. A catheter assembly also comprises an anchor balloon attached to the catheter at a distal end thereof, an ancillary balloon attached to the catheter at a point spaced in a proximal direction from the anchor balloon, a tube connecting the ancillary balloon to the anchor balloon so as to enable communication therebetween, and a flow stop mounted to the catheter for preventing fluid from returning to the tube from the anchor balloon upon a pressurization of the anchor balloon with fluid forced from the tube by an application of pressure to the ancillary balloon. A hollow catheter plug defining a flash chamber and having a transparent wall is connected to the catheter at a proximal end thereof for communicating with the catheter. A valve is connected to the plug for preventing fluid flow from the flash chamber.

U.S. Pat. No. 6,090,075 discloses a disposable self-lubricating catheterization assembly for inserting a catheter into the urethra of an individual for the purpose of evacuating the bladder. The catheter assembly includes a substantially rigid catheter introducer member for positioning the introducer against the urethral opening, a flexible catheter and a flexible thin-walled sheath surrounding the catheter introducer comprises a reservoir portion, a guide portion, lubricant and a membrane. The lubricant essentially fills the reservoir and is prevented by the membrane from prematurely coating the catheter, in order to facilitate grasping of the catheter and feeding of the tube along the urethra and into the bladder. A catheterization assembly in accordance with the present invention is suitable for use for self-catheterization and subsequent infection of the urinary tract. The improved easy-to-use disposable catheterization kit is also economically practical for use for temporary catheterization in hospitals, mobile emergency facilities, doctors' offices, rehabilitation facilities, nursing homes and the like.

Notwithstanding the prior art, the present invention is neither taught nor rendered obvious thereby.

SUMMARY OF THE INVENTION

The present invention relates to an ergonomic urological catheterization/irrigation tray. The tray includes a tray structure having a recessed area that includes at least a bottom, opposite side walls, a front and a back, wherein the front has a first width of a predetermined dimension and the back has a second width of a predetermined dimension less then the first width, such that the recessed area is wider at the front than it is at the back. The recessed area has at least one drain located at a lower area thereof. The tray further includes a top flange extending at least outwardly each of the opposite side walls, wherein a user may rest the flange on front upper portions of legs when in a supine position, and may discharge or be relieved into the tray.

The ergonomic urological catheterization/irrigation tray, in preferred embodiments, has a recessed area formed by the bottom, opposing sidewalls, front and back with a top view in a substantially trapezoidal shape.

In preferred embodiments, the present invention ergonomic urological catheterization/irrigation tray further includes at least two folding wing supports adapted to be folded into alignment with one of the opposing sidewalls, the front and the back, and adapted to be unfolded so as to be in a substantially horizontal orientation and extending outwardly from the tray for resting on front upper positions of legs. The at least two folding wing supports may be hingedly connected to the flange of the tray structure.

The ergonomic urological catheterization/irrigation tray wherein recessed area includes a divider wall creating two separate compartments. The divider wall has a minimum height that is less than minimum heights of all of the opposing sidewalls, the front and the back.

The ergonomic urological catheterization/irrigation tray wherein the at least two folding wing supports are hingedly connected to the flange of the tray structure, e.g. with hinge pins or unistructurally molded living hinges.

The ergonomic urological catheterization/irrigation tray kit wherein the at least two folding wing supports are hingedly connected to the back of the tray.

The ergonomic urological catheterization/irrigation tray wherein the at least two folding wing supports are hingedly connected to the front of the tray structure.

The ergonomic urological catheterization/irrigation tray wherein the tray has tapered sidewalls adapted to accommodate legs.

The ergonomic urological catheterization/irrigation tray kit wherein the bottom has non-flat topography.

The present invention also includes an ergonomic urological catheterization/irrigation tray kit. The kit includes:
 (a.) the tray described above;
 (b.) a Foley catheter;
 (c.) a urinary tract lubricant;
 (d.) surgical gloves;
 (e.) an inflation syringe for inflation of a catheter with fluid;
 (f.) irrigation syringe;
 (g.) evacuation tubing; and,
 (h.) antiseptic solutions.

BRIEF DESCRIPTION OF THE DRAWINGS

The present invention should be more fully understood when the specification herein is taken in conjunction with the drawings appended hereto wherein.

DETAILED DESCRIPTION OF THE PRESENT INVENTION

Figure 1:
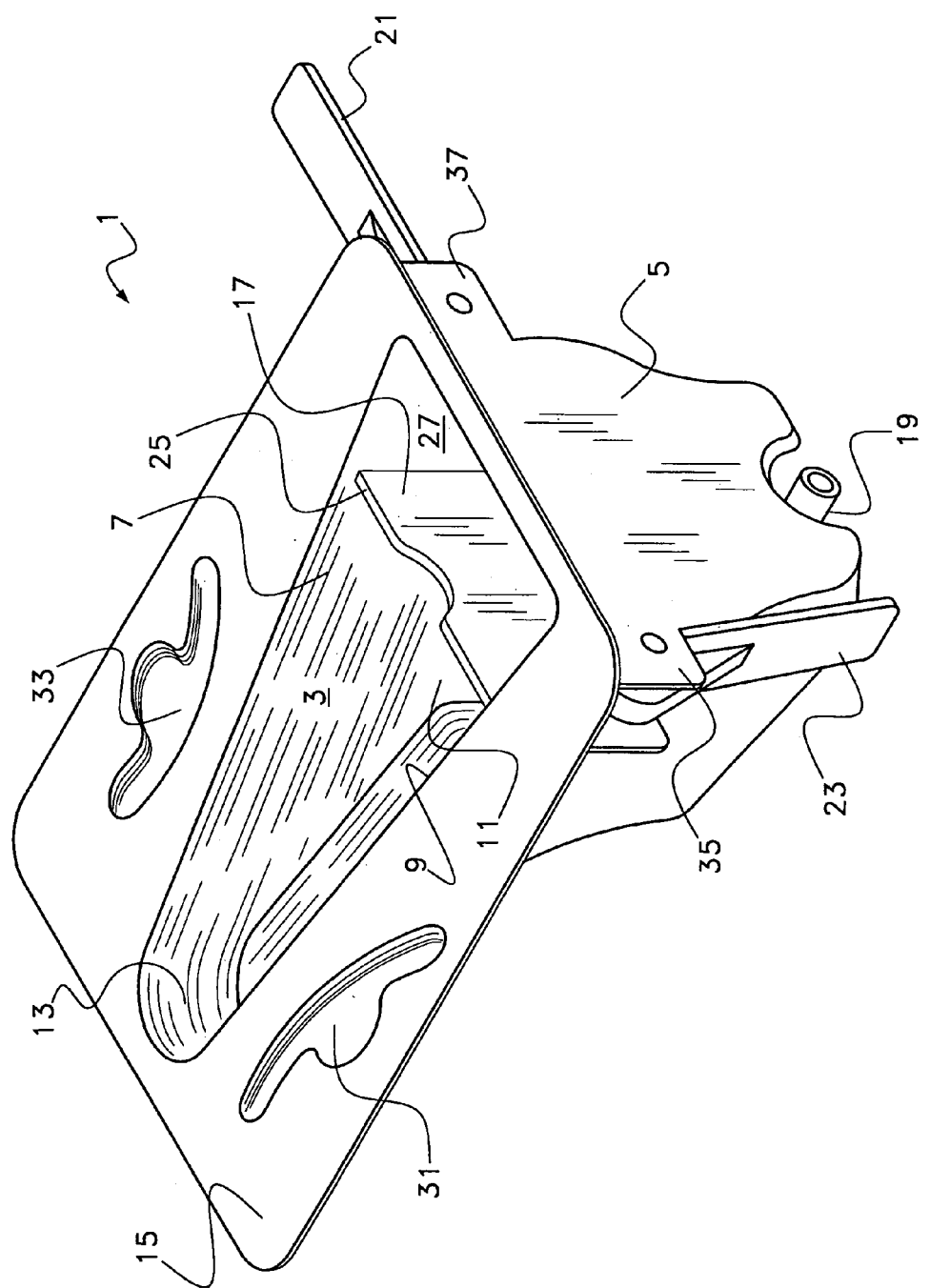
FIG. 1 shows a top oblique view of one embodiment of the present invention ergonomic urological catheterization/irrigation tray.
Figure 2:
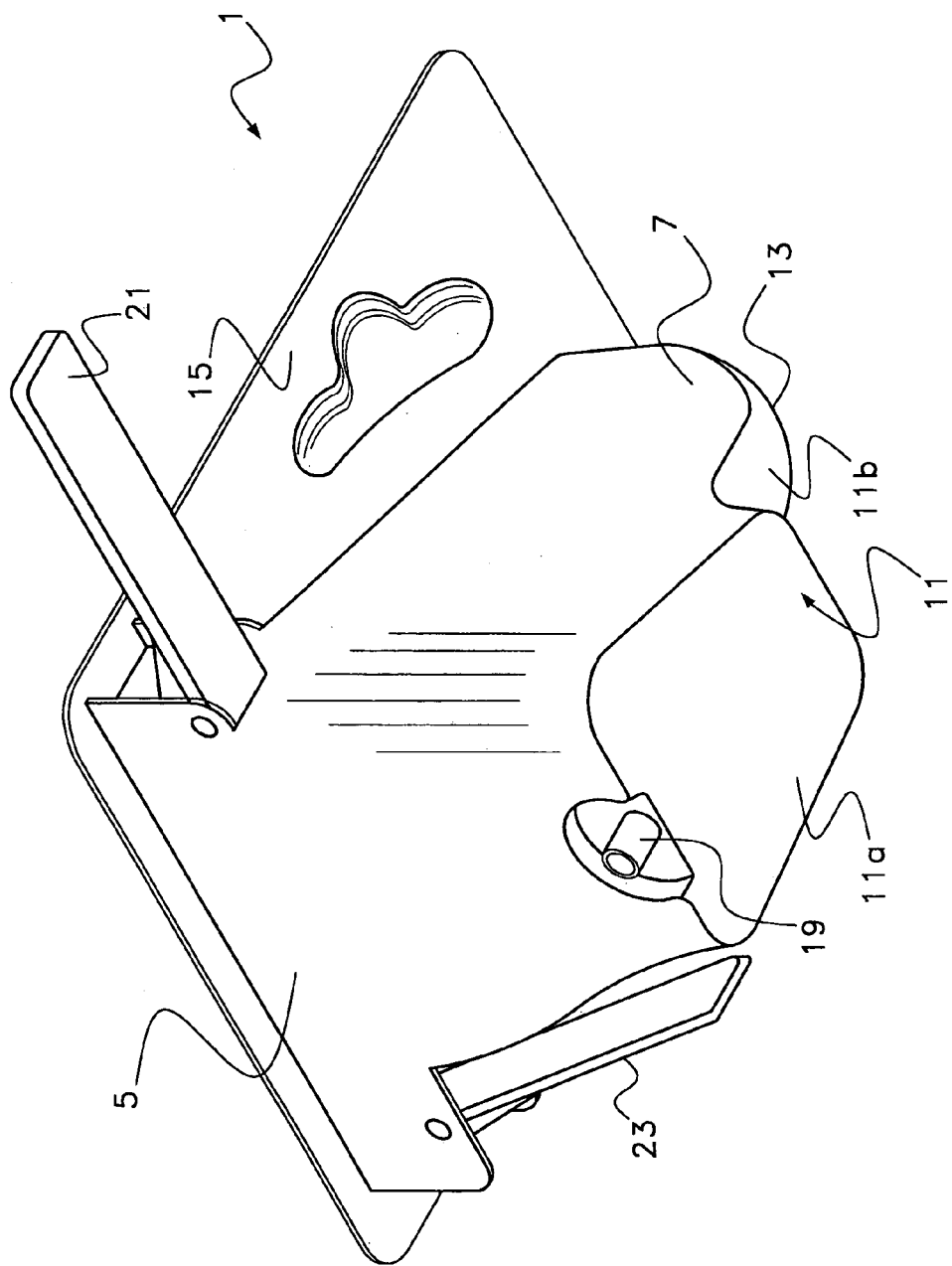
FIG. 2 shows a bottom oblique view of the present invention device shown in FIG. 1.
Figure 3:
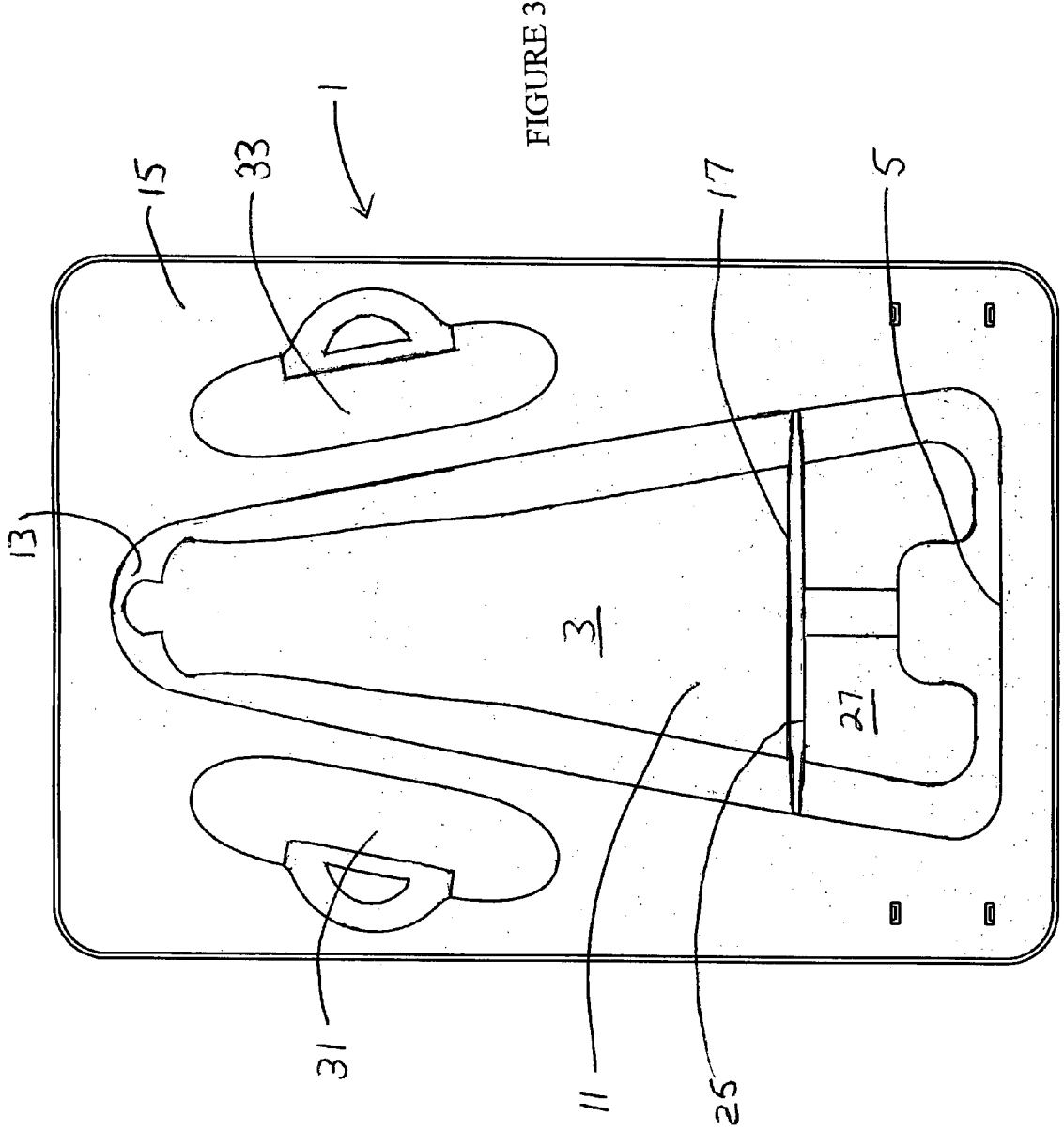
FIG. 3 shows a top view of the present invention device show in FIG. 1.
Figure 4:
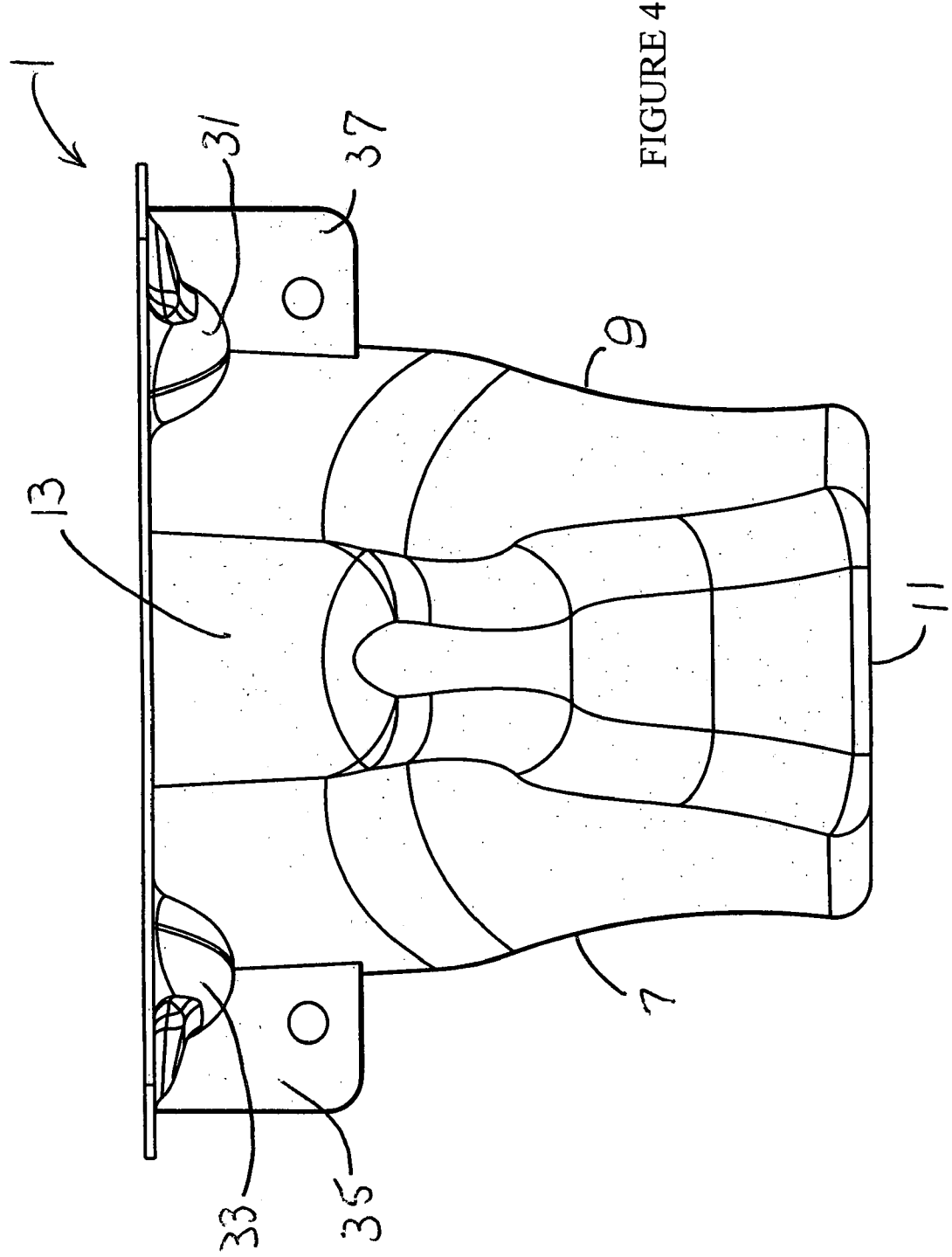
FIG. 4 illustrates a backend view of the present invention device shown in FIG. 1.
Figure 5:
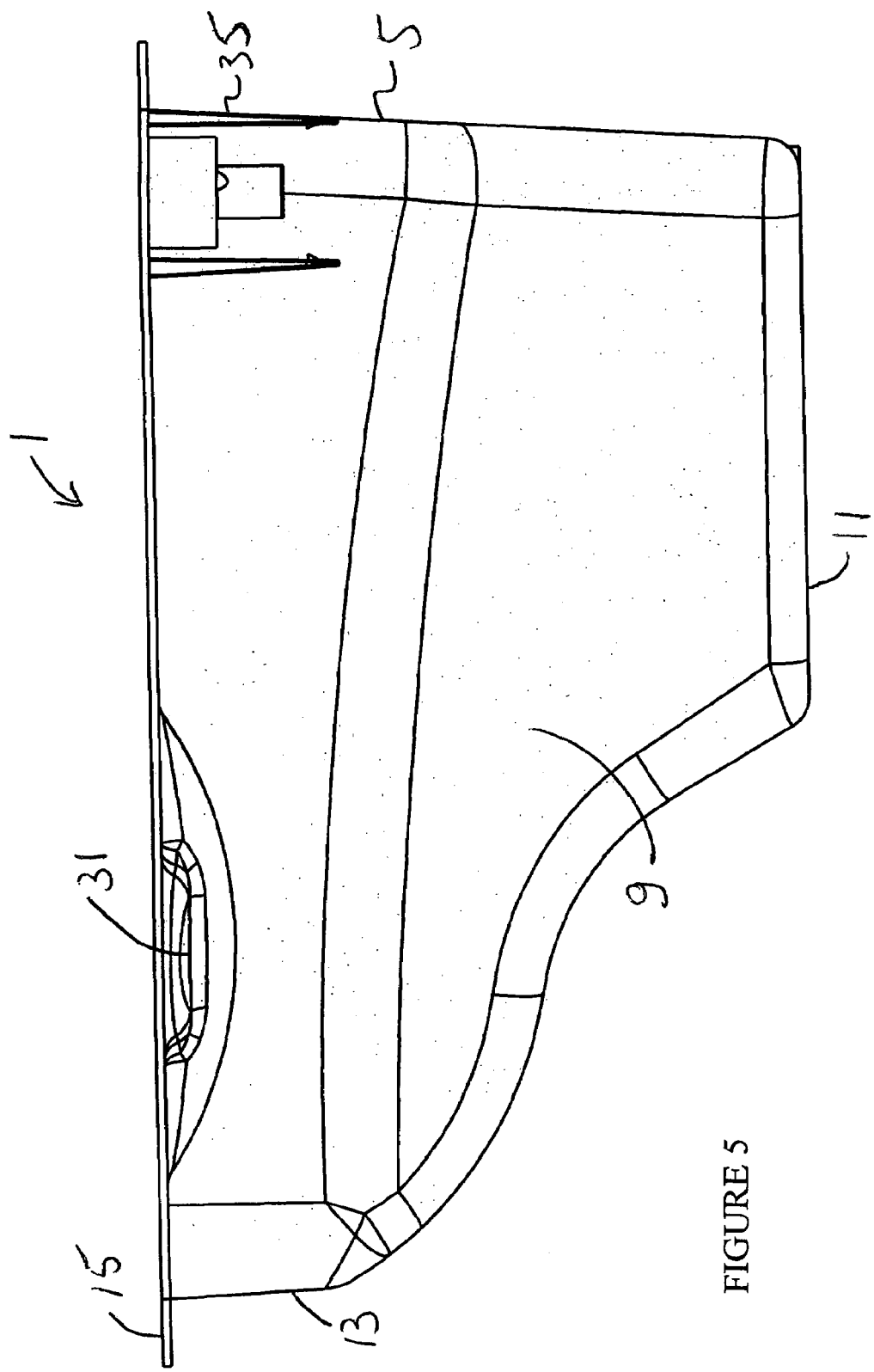
FIG. 5 illustrates a side view of the present invention device shown in FIG. 1.
Figure 6:
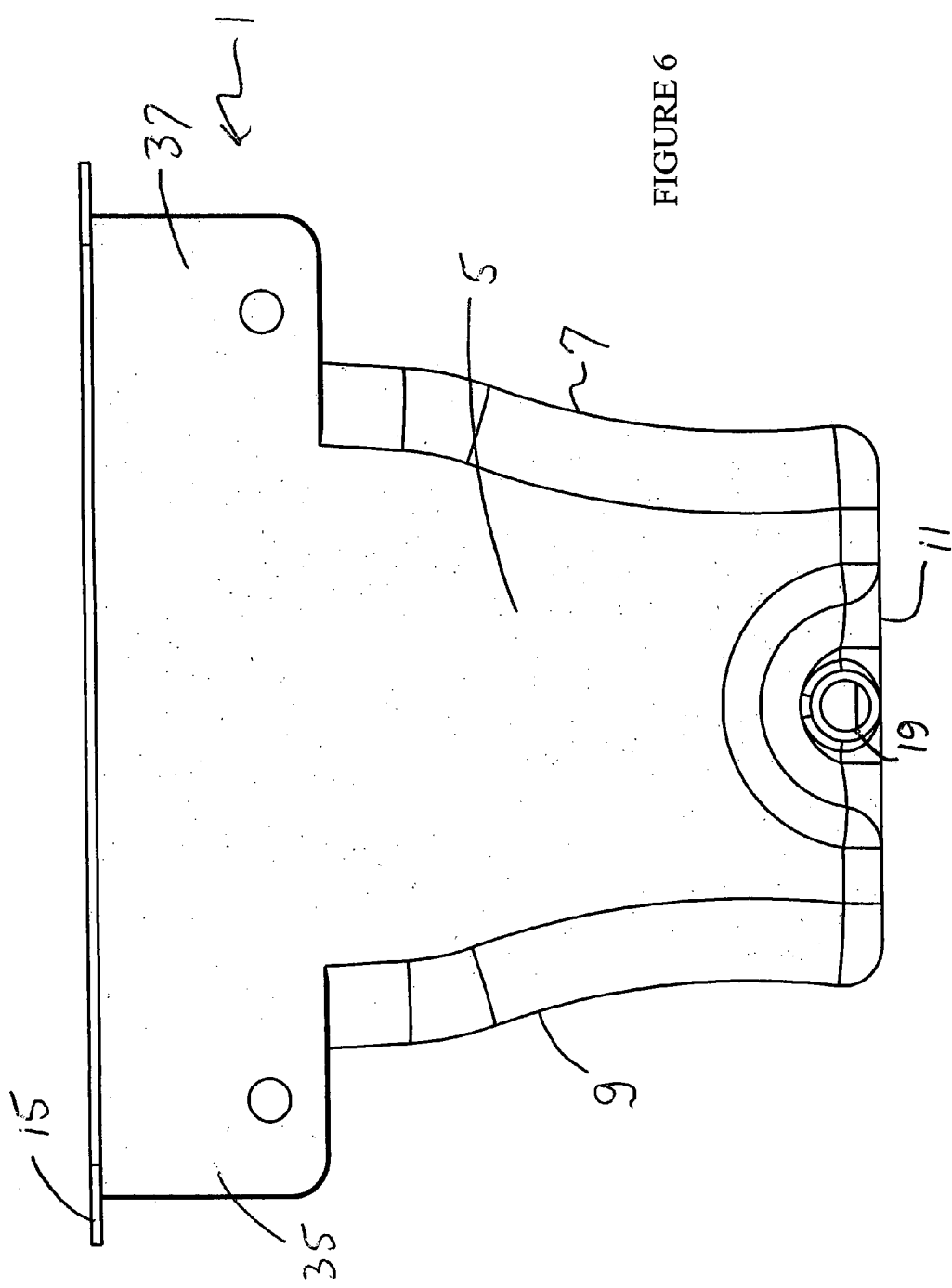
FIG. 6 shows a front view of the present invention device shown in FIG. 1.

FIG. 1, showing a top oblique view, FIG. 2 showing a bottom oblique view, FIG. 3 showing a top view, FIG. 4 showing a backend view, FIG. 5 showing a side view, FIG. 6 showing a front view, taken together illustrate a present invention catheterization/irrigation tray 1. It includes a recessed area 3 that includes a front 5, opposing side walls 7 and 9, bottom 11, back 13 and flange 15. The back 13 has a width that is significantly less than the width of front 5 such that opposing side walls 7 and 9 are non-parallel and tapered towards each other from front 5 to back 13. Thus, recessed area 3 has a generally trapezoidal footprint from a top view. Note also that, in this embodiment bottom 11 is not horizontally and, thus recessed area 3, has a non constant depth. In this embodiment bottom 11 has terraced arrangement with low area 11A and shallow area 11B (FIG. 2). Top flange 15 extends outwardly from opposing side walls 7 and 9 and acts in part so that a patient may have flange 15 rest on front upper portions of the patient's legs when in a seated position.

Optionally, but preferred, folding wing supports 21 and 23 are hingedly connected to side walls 7 and 9, respectively, and have two distinct positions. Wing support 21 is open so as to be substantially horizontally and wing support 23 is closed and thus in alignment with side wall 9. When not in use, both would be closed (folded down) and when in use would be opened. Drain 19 is located near bottom 11 for liquid drainage and may be directly connected to one or two drain holes in bottom 11. Drain 19 may be connected to flexible tubing and into a receiving receptance or safe drain, or may otherwise be used in accordance with acceptable standards and procedures. Optional divider wall 17 creates two separate compartments. The top 25 of divider wall 17 is lower than the top edges of recessed area 3. Thus, should fluids totally fill the volume behind divider wall 17, fluids will over flow into compartment 27 rather than spill over flange 15.

Optional Foley catheter lubricating wells 31 and 33 are available for right handed and left handed users so that lubricating material could be applied to the catheter or other insertion device by filling the well with lubricant and then sliding the device through the lubricant in the well.

A patient requiring an urological procedure may be positioned with tray 1 at back 13 below the scrotum and penis with flange 15 preventing the back portion of tray 1 from sliding or dropping downwardly between the patient's legs by resting the front upper portions of the legs while support wings 21 and 23 will perform a similar function for the front portion of tray 1. The surgeon will proceed to evacuate the bladder of its contents, urine and/or clots.

Figure 7:
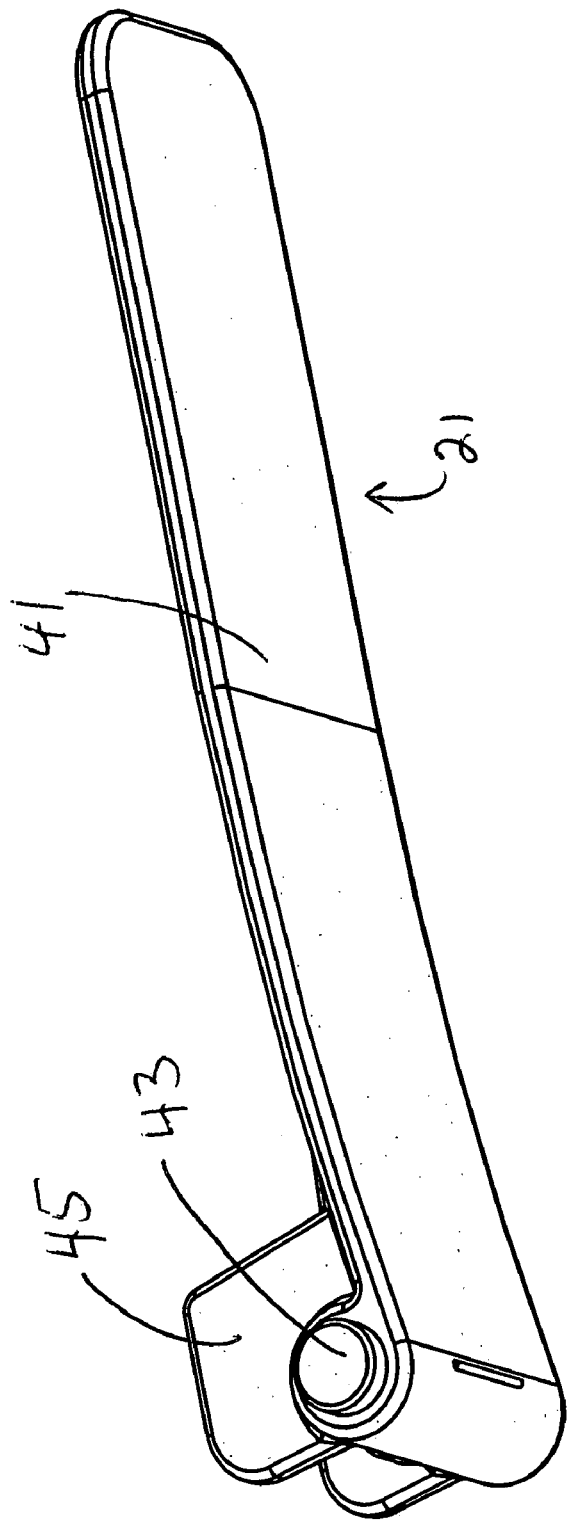
FIG. 7 shows a bottom oblique view of one embodiment of a support wing used with a present invention tray; and, FIG. 8 shows a top view of a present invention ergonomic urological catheterization/irrigation try kit.

Bracket sets 35 and 37 are integrally formed into the device with orifices adapted to receive the support wings. FIG. 7 shows support wing 21 from a bottom, oblique view in its open position, it includes, a main rest bar 41, pivot axle 43 that inserts directly into the orifices of the bracket sets and stops such as stop 45 to maintain a firm horizontal position when open.

Figure 8:
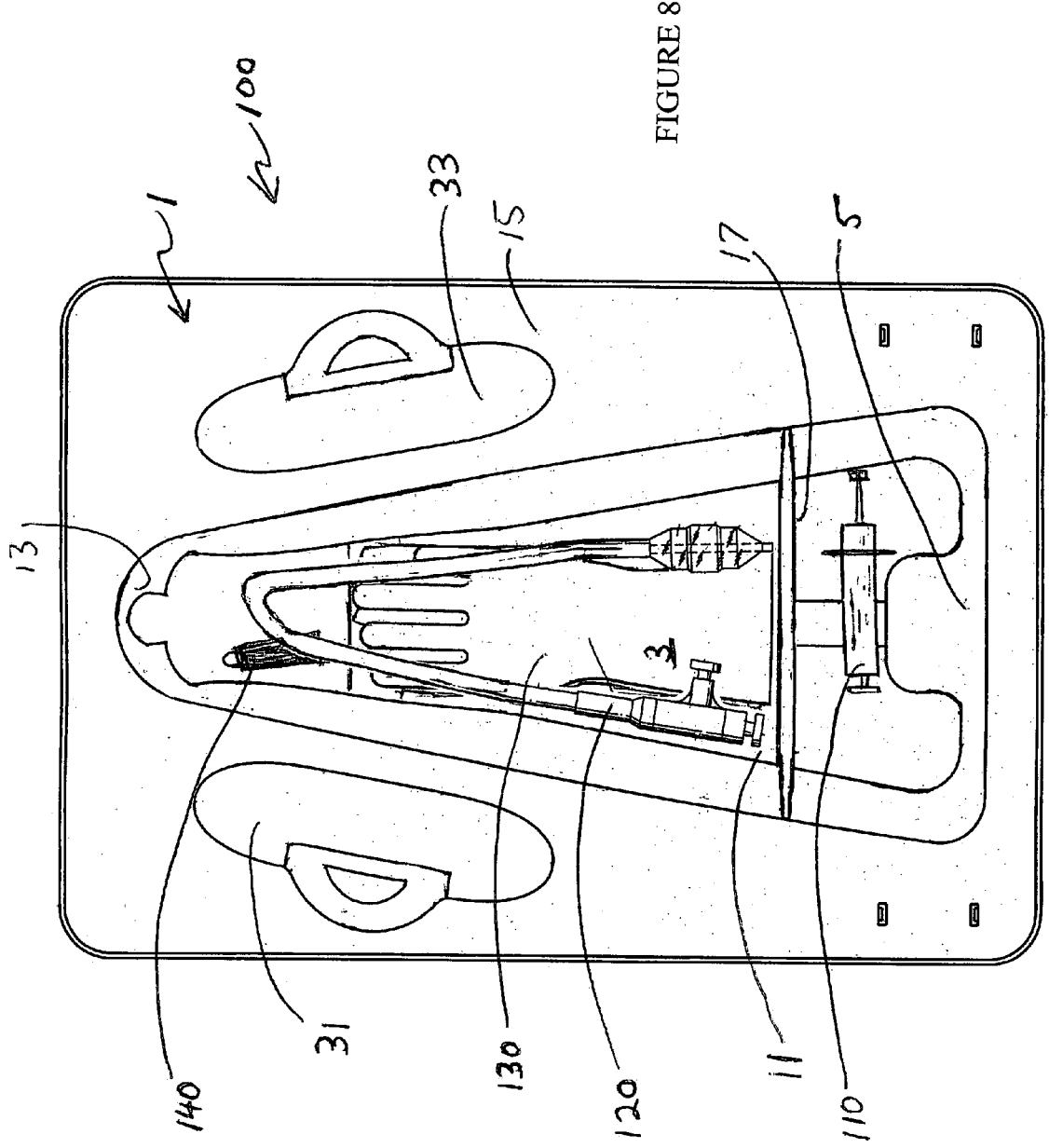

FIG. 8 shows a top view of the present invention kit 100. It includes tray 1 described above with identical components identically numbered. Also included is urinary tract inflation syringe 10, catheter 120, surgical gloves 130 and a tube of lubricant fluid 140. The kit is used as described generally above. The gloves being worn by the surgeon, the catheter being lubricated, inserted and then inflated with fluid using the syringe.

Obviously, numerous modifications and variations of the present invention are possible in light of the above teachings. It is therefore understood that within the scope of the appended claims, the invention may be practiced otherwise than as specifically described herein.

What is claimed is:

1. An ergonomic urological catheterization/irrigation tray which comprises:
 a tray structure having a recessed area that includes at least a bottom, opposite side walls, a front and back, wherein said front has a first width of a predetermined dimension and said back has a second width of a predetermined dimension less than said first width, such that said recessed area is wider at the front than it is at the back, said recessed area having at least one drain located at a lower area thereof, said tray including a flange extending outwardly from each of said opposing side walls, and including at least two folding wing supports adapted to be folded into alignment with one of said opposing sidewalls, said front and said back, and adapted to be unfolded so as to be in a substantially horizontal orientation and extending outwardly from said tray, wherein said flange and said wing supports are dimensioned and configured to rest on front upper portions of legs of a user when in a supine position, and to discharge or be relieved into said tray.

2. The ergonomic urological catheterization/irrigation tray of claim 1 wherein said tray recessed area formed by said bottom, opposing sidewalls, front and back has a top view trapezoidal shape.

3. The ergonomic urological catheterization/irrigation tray of claim 1 wherein said recessed area includes a divider wall creating two separate compartments to create an irrigation well and drainage well.

4. The ergonomic urological catheterization/irrigation tray of claim 3 wherein said divider wall has minimum height that is less than a minimum heights of all of said opposing sidewalls, said front and said back.

5. The ergonomic urological catheterization/irrigation tray of claim 1 wherein said at least two folding wing supports are hingedly connected to said flange of said tray structure.

6. The ergonomic urological catheterization/irrigation tray of claim 1 wherein said at least two folding wing supports are hingedly connected to said front of said tray structure.

7. The ergonomic urological catheterization/irrigation tray of claim 1 wherein said tray has tapered sidewalls adapted to accommodate legs.

8. The ergonomic urological catheterization/irrigation tray of claim 7 wherein said bottom has partially non-flat topography.

9. An ergonomic urological catheterization/irrigation tray which compromises:
 a tray structure having a recessed area that includes at least a bottom, opposite side walls, a front and back, wherein said front has a first width of a predetermined dimension and said back has a second width of a predetermined dimension less than said first width, such that said recessed area is wider at the front than it is at the back, said recessed area having at least one drain located at a lower area thereof, said tray including a flange extending outwardly from each of said opposing side walls, and including at least two folding wing supports adapted to be folded into alignment with one of said opposing sidewalls, said front and said back, and adapted to be unfolded so as to be in a substantially horizontal orientation and extending outwardly from said tray, wherein a user may rest said flange and said wing supports on front upper portions of legs when in a supine position, and my discharge or be relieved into said tray,
 and further wherein said support wings have living hinges.

10. The ergonomic urological catheterization/irrigation tray of claim 9 wherein said tray recessed area formed by said bottom, opposing sidewalls, front and back has a top view trapezoidal shape.

11. The ergonomic urological catheterization/irrigation tray of claim 9 wherein said recessed area includes a divider wall creating two separate compartments to create an irrigation well and drainage well.

12. The ergonomic urological catheterization/irrigation tray of claim 11 wherein said divider wall has minimum height that is less than a minimum heights of all of said opposing sidewalls, said front and said back.

13. The ergonomic urological catheterization/irrigation tray of claim 9 wherein said at least two folding wing supports are hingedly connected to said flange of said tray structure.

14. The ergonomic urological catheterization/irrigation tray of claim 9 wherein said at least two folding wing supports are hingedly connected to said front of said tray structure.

15. The ergonomic urological catheterization/irrigation tray of claim 9 wherein said tray has tapered sidewalls adapted to accommodate legs.

16. The ergonomic urological catheterization/irrigation tray of claim 15 wherein said bottom has partially non-flat topography.

* * * * *